(12) United States Patent
Adjaoute

(10) Patent No.: US 11,900,473 B2
(45) Date of Patent: *Feb. 13, 2024

(54) METHOD OF PERSONALIZING, INDIVIDUALIZING, AND AUTOMATING THE MANAGEMENT OF HEALTHCARE FRAUD-WASTE-ABUSE TO UNIQUE INDIVIDUAL HEALTHCARE PROVIDERS

(71) Applicant: Brighterion, Inc., Purchase, NY (US)

(72) Inventor: Akli Adjaoute, Mill Valley, CA (US)

(73) Assignee: Brighterion, Inc., Purchase, NY (US)

( * ) Notice: Subject to any disclaimer, the term of this patent is extended or adjusted under 35 U.S.C. 154(b) by 213 days.

This patent is subject to a terminal disclaimer.

(21) Appl. No.: 17/364,450

(22) Filed: Jun. 30, 2021

(65) Prior Publication Data

US 2021/0326999 A1    Oct. 21, 2021

Related U.S. Application Data

(63) Continuation of application No. 16/677,458, filed on Nov. 7, 2019, now Pat. No. 11,080,793, which is a continuation of application No. 14/986,534, filed on Dec. 31, 2015, now Pat. No. 10,546,099, which is a continuation-in-part of application No. 14/815,848, (Continued)

(51) Int. Cl.
| | |
|---|---|
| *G06Q 40/08* | (2012.01) |
| *G16H 40/20* | (2018.01) |
| *G06Q 10/10* | (2023.01) |
| *G06N 20/00* | (2019.01) |

(52) U.S. Cl.
CPC .............. *G06Q 40/08* (2013.01); *G06Q 10/10* (2013.01); *G16H 40/20* (2018.01); *G06N 20/00* (2019.01); *Y02A 90/10* (2018.01)

(58) Field of Classification Search
CPC ...................................................... G06Q 50/22
See application file for complete search history.

(56) References Cited

U.S. PATENT DOCUMENTS

| | | |
|---|---|---|
| 7,159,208 B2 | 1/2007 | Keeley |
| 7,590,970 B2 | 9/2009 | Bromley |

(Continued)

OTHER PUBLICATIONS

Office Action from U.S. Appl. No. 16/299,998 dated Aug. 18, 2022.
(Continued)

*Primary Examiner* — Ojo O Oyebisi
(74) *Attorney, Agent, or Firm* — Hovey Williams LLP

(57) ABSTRACT

A method of preventing healthcare fraud-waste-abuse uses artificial intelligence machines to limit financial losses. Healthcare payment request claims are analyzed by predictive models and their behavioral details are compared to running profiles unique to each healthcare provider submitting the claims. A decision results that the instant healthcare payment request claim is or is not fraudulent-wasteful-abusive. If it is, a second analysis of a group behavioral in which the healthcare provider is clustered using unsupervised learning algorithms and compared to a running profile unique to each group of healthcare providers submitting the claims. An overriding decision results if the instant healthcare payment request claim is or is not fraudulent-wasteful-abusive according to group behavior.

17 Claims, 4 Drawing Sheets

Related U.S. Application Data filed on Jul. 31, 2015, now abandoned, which is a continuation-in-part of application No. 14/514,381, filed on Oct. 15, 2014, now abandoned, said application No. 14/986,534 is a continuation-in-part of application No. 14/521,667, filed on Oct. 23, 2014, now abandoned, and a continuation-in-part of application No. 14/815,934, filed on Jul. 31, 2015, now abandoned, and a continuation-in-part of application No. 14/517,771, filed on Oct. 17, 2014, now abandoned, and a continuation-in-part of application No. 14/517,872, filed on Oct. 19, 2014, now abandoned, and a continuation-in-part of application No. 14/935,742, filed on Nov. 9, 2015, now abandoned.

(56) References Cited

U.S. PATENT DOCUMENTS

| | | |
|---|---|---|
| 7,630,956 B2 | 12/2009 | Wyatt et al. |
| 7,685,083 B2 | 3/2010 | Fairweather |
| 7,877,421 B2 | 1/2011 | Berger et al. |
| 8,401,990 B2 | 3/2013 | Silsby |
| 9,069,737 B1 | 6/2015 | Kimotho et al. |
| 9,134,215 B1 | 9/2015 | Vignisson et al. |
| 9,996,694 B2 | 6/2018 | Sethumadhavan et al. |
| 10,817,530 B2 | 10/2020 | Siebel et al. |
| 2002/0147754 A1 | 10/2002 | Dempsey et al. |
| 2006/0171509 A1 | 8/2006 | Berthaud et al. |
| 2007/0239936 A1 | 10/2007 | Gluhovsky |
| 2013/0290317 A1 | 10/2013 | Spivack et al. |
| 2014/0058914 A1 | 2/2014 | Song et al. |
| 2014/0149128 A1* | 5/2014 | Getchius ............... G16H 50/20 705/2 |
| 2015/0100568 A1 | 4/2015 | Golden et al. |
| 2017/0006135 A1 | 1/2017 | Siebel et al. |
| 2017/0289176 A1 | 10/2017 | Chen et al. |
| 2018/0032723 A1 | 2/2018 | Danger et al. |
| 2019/0007517 A1 | 1/2019 | Jagannath et al. |

OTHER PUBLICATIONS

Office Action From U.S. Appl. No. 17/341,459 dated Jul. 22, 2022.
Office Action From U.S. Appl. No. 16/264,144 dated Aug. 25, 2022.
Office Action From U.S. Appl. No. 16/424,187 dated Sep. 2, 2022.
Office Action from U.S. Appl. No. 16/168,566 (dated Jul. 21, 2021).
Office Action from U.S. Appl. No. 16/264,144 (dated Sep. 22, 2021).
Office Action from U.S. Appl. No. 16/424,187 (dated Sep. 1, 2021).
Office Action from U.S. Appl. No. 16/663,452 (dated Aug. 17, 2021).
Office Action from U.S. Appl. No. 16/743,009 (dated Sep. 10, 2021).
Office Action From U.S. Appl. No. 16/299,998 dated Dec. 23, 2022.
Office Action From U.S. Appl. No. 17/200,997 dated Feb. 2, 2023.
Office Action From U.S. Appl. No. 17/085,109 dated Dec. 8, 2022.
Office Action From U.S. Appl. No. 17/198,473 dated Feb. 15, 2023.
Office Action from U.S. Appl. No. 16/168,566 (dated Mar. 23, 2021).
Office Action from U.S. Appl. No. 16/226,246 (dated Apr. 26, 2021).
Office Action from U.S. Appl. No. 16/264,144 (dated Apr. 23, 2021).
Office Action from U.S. Appl. No. 16/663,452 (dated Mar. 12, 2021).
Office Action from U.S. Appl. No. 16/743,009 (dated Mar. 24, 2021).
Office Action From U.S. Appl. No. 16/424,187 (dated Apr. 26, 2022).
Office Action From U.S. Appl. No. 16/264,144 (dated Apr. 13, 2022).
Office Action From U.S. Appl. No. 16/424,187 (dated Dec. 9, 2021).
Office Action From U.S. Appl. No. 16/743,009 (dated Jan. 28, 2022).
Office Action From U.S. Appl. No. 16/424,187 dated Feb. 24, 2023.
Office Action From U.S. Appl. No. 17/153,013 dated Mar. 2, 2023.
Office Action From U.S. Appl. No. 17/364,319 dated Mar. 9, 2023.
Office Action From U.S. Appl. No. 17/992,672 dated Mar. 10, 2023.
Office Action From U.S. Appl. No. 16/299,998 dated Apr. 13, 2023.

* cited by examiner

METHOD OF PERSONALIZING, INDIVIDUALIZING, AND AUTOMATING THE MANAGEMENT OF HEALTHCARE FRAUD-WASTE-ABUSE TO UNIQUE INDIVIDUAL HEALTHCARE PROVIDERS

RELATED APPLICATIONS

The current patent application is a continuation patent application which claims priority benefit with regard to all common subject matter to identically-titled U.S. patent application Ser. No. 16/677,458, filed Nov. 7, 2019, which, itself, is a continuation of identically-titled U.S. patent application Ser. No. 14/986,534, filed Dec. 31, 2015 (issued as U.S. Pat. No. 10,546,099), which, itself, is: (A) a continuation-in-part application of and claims priority benefit with regard to all common subject matter to U.S. patent application Ser. No. 14/815,848, filed Jul. 31, 2015, entitled AUTOMATION TOOL DEVELOPMENT METHOD FOR BUILDING COMPUTER FRAUD MANAGEMENT APPLICATIONS, which, itself, is a continuation-in-part application of and claims priority benefit with regard to all common subject matter to U.S. patent application Ser. No. 14/514,381, filed Oct. 15, 2014, and entitled ARTIFICIAL INTELLIGENCE FRAUD MANAGEMENT SOLUTION; (B) a continuation-in-part application of and claims priority benefit with regard to all common subject matter to U.S. patent application Ser. No. 14/521,667, filed Oct. 23, 2014, and entitled BEHAVIOR TRACKING SMART AGENTS FOR ARTIFICIAL INTELLIGENCE FRAUD PROTECTION AND MANAGEMENT; (C) a continuation-in-part application of and claims priority benefit with regard to all common subject matter to U.S. patent application Ser. No. 14/815,934, filed Jul. 31, 2015, entitled METHOD FOR DETECTING MERCHANT DATA BREACHES WITH A COMPUTER NETWORK SERVER; (D) a continuation-in-part application of and claims priority benefit with regard to all common subject matter to U.S. patent application Ser. No. 14/517,771, filed Oct. 17, 2014, entitled REAL-TIME CROSS-CHANNEL FRAUD PROTECTION; (E) a continuation-in-part application of and claims priority benefit with regard to all common subject matter to U.S. patent application Ser. No. 14/517,872, filed Oct. 19, 2014, entitled HEALTHCARE FRAUD PROTECTION AND MANAGEMENT; and (F) a continuation-in-part application of and claims priority benefit with regard to all common subject matter to U.S. patent application Ser. No. 14/935,742, filed Nov. 9, 2015, entitled DATA CLEAN-UP METHOD FOR IMPROVING PREDICTIVE MODEL TRAINING. The listed earlier-filed non-provisional applications are hereby incorporated by reference in their entireties into the current patent application.

BACKGROUND OF THE INVENTION

Field of the Invention

The present invention relates to methods of preventing healthcare fraud-waste-abuse and more specifically to employing artificial intelligence machines to limit financial losses and detecting unwarranted reimbursements.

Background

Healthcare fraud, waste, and abuse have blossomed in recent years because deep pockets like the Government and large insurance companies are now more than ever paying all the bills.

Insurance Companies and Government quite obviously try to control fraud, waste, and abuse, but their third party, after-the-fact status to medical treatments makes them less able and less effective in controlling this kind of fraud. Hospitals, clinics, pharmaceutical companies, and other healthcare providers in general have stepped in to exploit these inadequacies. Costs, as a direct result have spiraled beyond all reason.

Medicare fraud is legally defined to include knowingly and willfully executing, or attempting to execute, a scheme or ploy to defraud the Medicare program, or obtaining information by means of false pretenses, deception, or misrepresentation in order to receive inappropriate payment from the Medicare program. The most frequent kinds of fraud are false statements and misrepresentations of entitlement or payment under the Medicare program.

The Centers for Medicare & Medicaid Services (CMMS) defines the kind of fraud they fight as "the intentional deception or misrepresentation that the individual knows to be false or does not believe to be true, and the individual makes knowing that the deception could result in some unauthorized benefit to himself or herself or some other person."

Presumably, the vast majority of government contractors who provide goods and services to the government are honest, as are most vendors serving private purchasers. Nevertheless, even a small fraction amounts to a substantial level fraud is directed at the Government, and thereby all of us.

The particular kinds of healthcare fraud we all suffer from includes:
Upcoding, which is the reporting of inappropriate diagnoses or procedures to increase profits;
Billing for services not actually furnished;
Duplicate billings for the same services or supplies;
Misrepresenting dates and misdescribing services furnished or misidentifying the beneficiaries;
Billing for non-covered or non-chargeable services as if they were covered and chargeable items;
Misallocating costs on reports, such as including costs of non-covered services, supplies, or equipment in allowable costs;
Providers colluding with employees, independent contractors, suppliers, and others to overcharge the program through various devices (commissions, fee splitting) to siphon-off or conceal illegal profits;
Billing Medicare for costs not actually sustained or which arose from non-program activities, other enterprises, or personal expenses;
Repeatedly including unallowable cost items on a provider's cost report (except for purposes of establishing a basis for appeal);
Manipulating measurements to obtain bonus payments, such as increasing the square footage of their outpatient areas on paper;
Amounts paid to owners or administrators that have been determined to be excessive in prior cost report settlements;
Days that have been improperly reported and would result in an overpayment if not adjusted;
Depreciation methods not approved by Medicare;
Altering claim forms to obtain a higher payment amount;
Billing twice for the same service or item;
Billing separately for services that should be included in a single service fee;
Misrepresenting the diagnosis to justify payment;

Continuing to bill for services or items no longer medically necessary;
Billing for rental equipment after date of return
Billing "non-covered" services or items as "covered" services;
Ordering unnecessary lab tests;
Using another person's Medicare card to obtain;
Waiving co-insurance or deductible;
Billing for home health care services for patients who do not meet the requirement of "homebound" status;
Billing social activities as psychotherapy;
Billing group services as individual services for each patient in the group;
Number of day stays in hospital and Discharge and readmission to same hospital;
Diagnosis-related group analysis and payment window.

Physicians or other healthcare practitioners are obvious cradles of healthcare fraud, but healthcare fraud wrongdoers also include:
Suppliers of durable medical equipment;
An employee of a physician or supplier;
An employee of the companies that manage Medicare billing;
A billing service;
A beneficiary; and
Other people and businesses in a position to bill a Medicare program or to benefit from the Medicare billing.

Better methods to combat fraud, waste and abuse, information are not limited to that included in the claims. The most useful kinds of supplemental information include non-claims based utilization data or actual clinical data from an EMR, and Pharmacy claims or transactions.

Improvements in detecting waste and abuse in healthcare will require a different approach, a comprehensive rethinking of the waste and abuse crisis. Waste, fraud, and leakage in the industry is the major problem. Illegal activity, while significant in absolute numbers, is trivial when compared to $2.8T in annual healthcare spending. Solutions must focus on the breadth of leakage. For example, a simple excessive billing of preventive visits (Evaluation and Management claims) results in $20-$30 additional billed per visit. With one billion primary care physician visits each year, that kind of leakage is larger than the entire fraud recoveries for the market in a single year.

Almost all conventional analytic solutions, operate within extremely rigid boundaries, even those that propose to be non-hypothesis based. They are either designed or tuned to look at various scenarios in such a way that they will only catch a limited range of leakage problems. When something truly surprising happens, or variation occurs that is not anticipated, these models prove to be worthless.

Working solutions require a new approach, new algorithms and models that are not already trained or constrained within the boundaries of known scenarios. Technology that is designed to aggregate scenarios to get at large leakage issues easily and identify systemic issues that plague the system. Highly trained "eyes" are needed on the data output that can process raw data rapidly and efficiently.

SUMMARY OF THE INVENTION

Briefly, a method embodiment of the present invention of preventing healthcare fraud-waste-abuse uses artificial intelligence machines to limit financial losses. Healthcare payment request claims are analyzed by predictive models and their behavioral details are compared to running profiles unique to each healthcare provider submitting the claims. A decision results that the healthcare payment request claim is or is not fraudulent-wasteful-abusive. If it is, a second analysis of a group behavioral in which the healthcare provider is clustered is compared to a running profile unique to each group of healthcare providers submitting the claims. An overriding decision results if the instant healthcare payment request claim is not fraudulent-wasteful-abusive according to group behavior.

The above and still further objects, features, and advantages of the present invention will become apparent upon consideration of the following detailed description of specific embodiments thereof, especially when taken in conjunction with the accompanying drawings.

DETAILED DESCRIPTION OF THE INVENTION

Method embodiments of the present invention leverage artificial intelligence machines in the prevention of healthcare fraud-waste-abuse by individual and groups of providers submitting payment claims. My earlier U.S. patent application, Ser. No. 14/517,872, filed Oct. 19, 2014, titled, HEALTHCARE FRAUD PROTECTION AND MANAGEMENT, is incorporated in full herein by reference.

Figure 1:
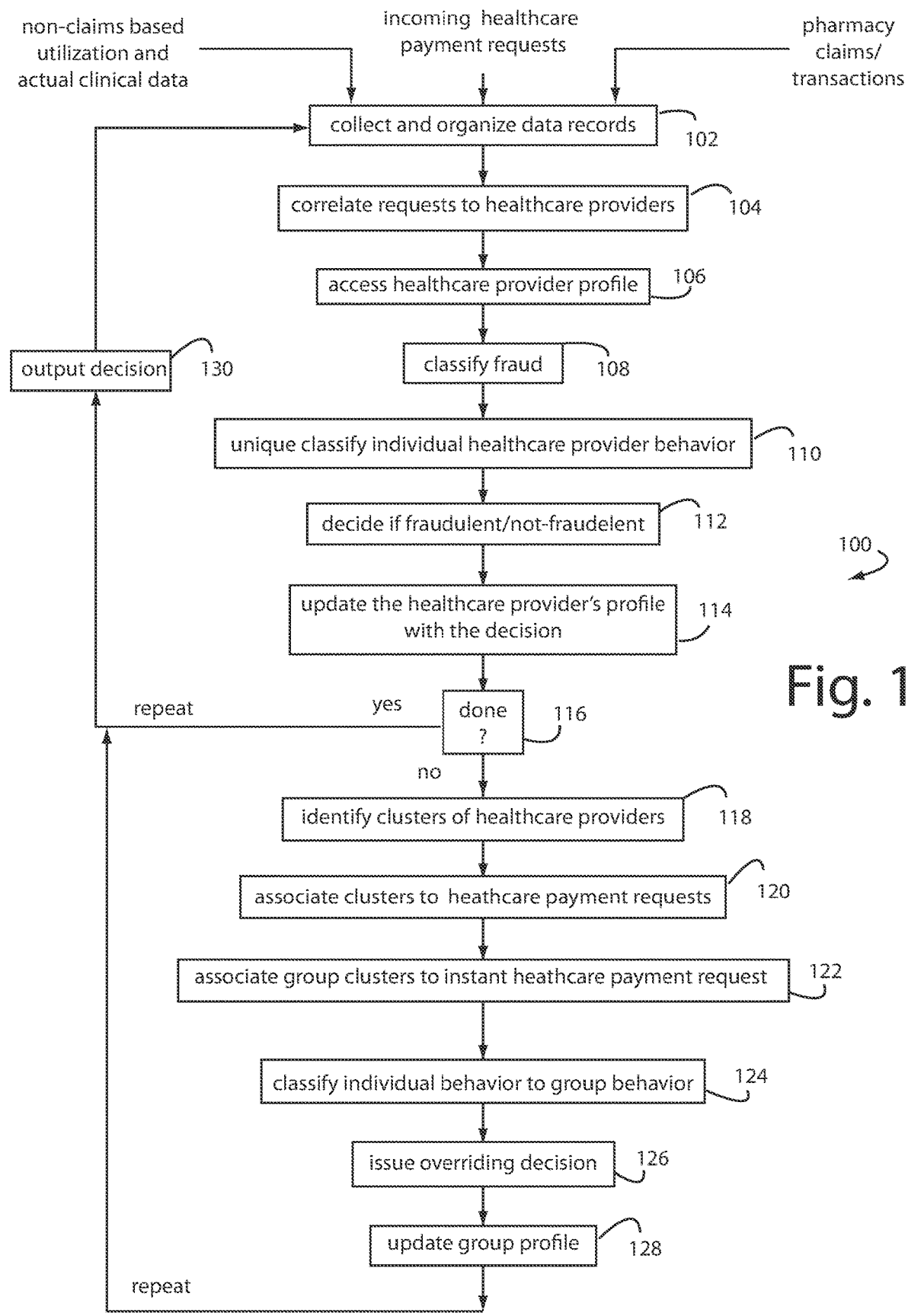
FIG. 1 is a flowchart diagram of a method embodiment of the present invention of healthcare fraud-waste-abuse management that depends on an artificial intelligence machine to complete its several steps.

FIG. 1 represents a method embodiment of the present invention of healthcare fraud-waste-abuse management that depends on an artificial intelligence machine to complete its several steps, and is referred to herein by the general reference numeral 100. A first step 102 collects and organizes incoming streams of data from a variety of healthcare providers. A processor connected to a network executes an algorithm to contemporaneously receive healthcare payment request claim data, non-claim based utilization data, actual clinical data, and pharmacy claim or transaction data as records. An algorithm is executed by the processor to store the data records in a computer memory storage device. Another algorithm sorts through the discrete data fields and payload data in each such data record.

I describe a data cleanup method in my U.S. patent application, Ser. No. 14/935,742, DATA CLEAN-UP METHOD FOR IMPROVING PREDICTIVE MODEL TRAINING, filed Nov. 9, 2015, that would be useful in harmonizing and trimming away irrelevant, excess, and useless information received in these data records. I also describe a data enrichment method in my U.S. patent application Ser. No. 14/941,586, METHOD OF OPERATING ARTIFICIAL INTELLIGENCE MACHINES TO IMPROVE PREDICTIVE MODEL TRAINING AND PERFORMANCE, filed Nov. 14, 2015, that describes how the healthcare payment request claim data, non-claim based utilization data, actual clinical data, and pharmacy claim or transaction data records can be usefully combined to improve the performance of predictive models and smart agent profiling. Both such United States Patent Applications are parents to this continuation-in-part application that also continues-in-part from the HEALTHCARE FRAUD PROTECTION AND MANAGEMENT Patent Application.

A key descriptive attribute in widespread use in the healthcare field is the Diagnosis Related Group (DRG) code. This 3-digit code helps to organize diagnoses and procedures into clinically cohesive groups that demonstrate similar consumption of hospital resources. It is a rough form of fuzzification that can help artificial intelligence machines deal with unimportant nuances in data through a sort of clustering of statistical information. In general, fuzzification is a process of transforming crisp values into grades of membership, e.g., infants 0-1, toddlers 2-5, children 6-12, teenagers 13-19, and adults 20+. The healthcare attributes that properly contribute to a particular DRG classification are well understood. Odd value or simply odd, abnormal attributes that coexist in a healthcare payment claim with a proffered DRG are symptomatic of fraud. So when a predictive model like a decision tree or a case-based reasoning classifies a different DRG that the proffered one, then fraud is a likely culprit.

The healthcare providers are correlated in a step 104 to particular ones of the incoming healthcare payment request claims with the processor and an algorithm that generates and maintains a unique smart agent profile in the computer memory storage device for each healthcare provider. An example of this correlation is represented in FIG. 11 of the previously mentioned Patent Application (METHOD OF OPERATING ARTIFICIAL INTELLIGENCE MACHINES TO IMPROVE PREDICTIVE MODEL TRAINING AND PERFORMANCE) as items 1102-1114.

A healthcare provider profile uniquely associated with an healthcare provider is accessed in a step 106 with the processor and an algorithm that compares the unique smart agent profile to an instant incoming healthcare payment request claim.

Particular ones of the incoming healthcare payment request claims are classified in a step 108 according to a fraud-waste-abuse criteria with the processor and an algorithm that includes a predictive model trained on an accumulation of supervised and unsupervised healthcare payment request claims previously submitted by essentially the same healthcare providers. And particular ones of the incoming healthcare payment request claims are classified in a step 110 with the processor and an algorithm that applies a unique individual behavior criteria based on a comparison of an individual's past behaviors extracted and recorded in their unique healthcare provider profile and an instant behavior evident in the instant incoming healthcare payment request claim stored in the computer memory storage device.

A decision is issued in a step 112 with the processor and an algorithm that decides an instant healthcare payment request claim is fraudulent-wasteful-abusive or not-fraudulent-wasteful-abusive based on a combination of a fraud-waste-abuse criteria classification and a unique individual behavior criteria classification stored in the computer memory storage device.

A unique healthcare provider profile of each healthcare provider stored in the computer memory storage device is updated with the decision in a step 114.

Steps 102-114 are then repeated as more incoming healthcare payment request claim records are received. If a step 116 decides the process is done, e.g., the instant payment request claim was judged non-fraudulent.

Deviant individual behaviors judged as fraudulent-wasteful-abusive may nevertheless be non-fraudulent-wasteful-abusive even though an individual behavioral analysis classifies an instant incoming healthcare payment request claim that way. If clustering identifies the individual as belonging to a group, and the instant behavior is consistent with behavior profiles maintained for that group, then the instant incoming healthcare payment request claim may be more properly classified with a decision that it is non-fraudulent. In order to implement this, the method continues with more steps.

Clusters of healthcare providers that share a group behavior are identified in a step 118.

Groups of healthcare providers are associated to particular ones of the incoming healthcare payment request claims in a step 120.

A healthcare provider profile uniquely associated with a group of healthcare providers is accessed in a step 122 and compared to an instant incoming healthcare payment request claim.

Particular ones of the incoming healthcare payment request claims are classified in a step 124 according to a group-behavior criteria and based on a comparison of past behaviors extracted and recorded in their unique healthcare provider profile and an instant behavior evident in the instant incoming healthcare payment request claim.

An overriding decision is issued in a step 126 with the processor and an algorithm that decides an instant healthcare payment request claim is fraudulent-wasteful-abusive or not-fraudulent-wasteful-abusive based on a combination of a fraud-waste-abuse criteria classification and a group behavior criteria classification stored in the computer memory storage device.

A unique healthcare provider profile of each group of healthcare providers stored in the computer memory storage device is updated with the overriding decision in a step 128.

Figure 2:
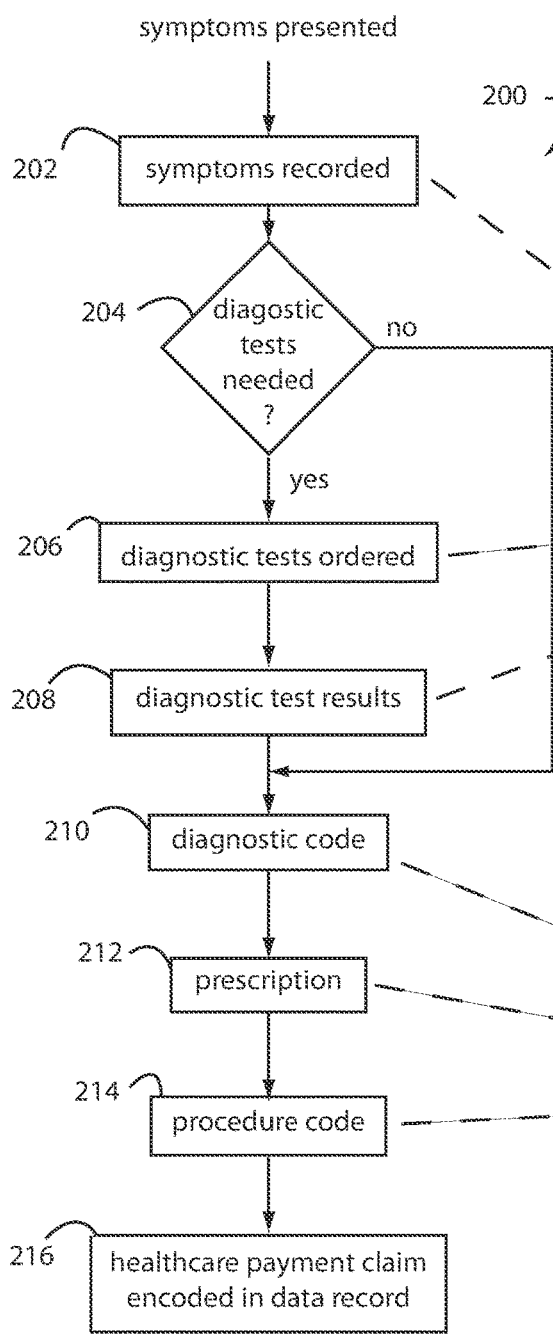
FIG. 2 is a flowchart diagram of a healthcare provider claiming method in which a patient presents a collection of symptoms.

FIG. 2 represents a healthcare provider claiming method 200 in which a patient presents a collection of symptoms. A step 202 records these symptoms. A test 204 asks if the recorded symptoms are sufficient to make a diagnosis. If not, diagnostic tests are ordered in a step 206. A step 208 gets the diagnostic test results. A diagnostic code is decided by the healthcare provider and entered in payment claim in a step 210.

Step 210 represents an opportunity for a fraudulent coding, e.g., one that does not comport with the symptoms recorded in step 202 and the diagnostic test results in step 208. Any prescriptions needed are written in a step 212. A procedure code is entered in a step 214. Step 214 represents another opportunity for fraudulent coding, e.g., a procedure that does not comport with the diagnostic code recorded in step 210. A step 216 represents an encoding by the healthcare provider of the payment claim. These represent the many payment claims received by step 102 in FIG. 1 submitted by millions of healthcare providers.

Figure 3:
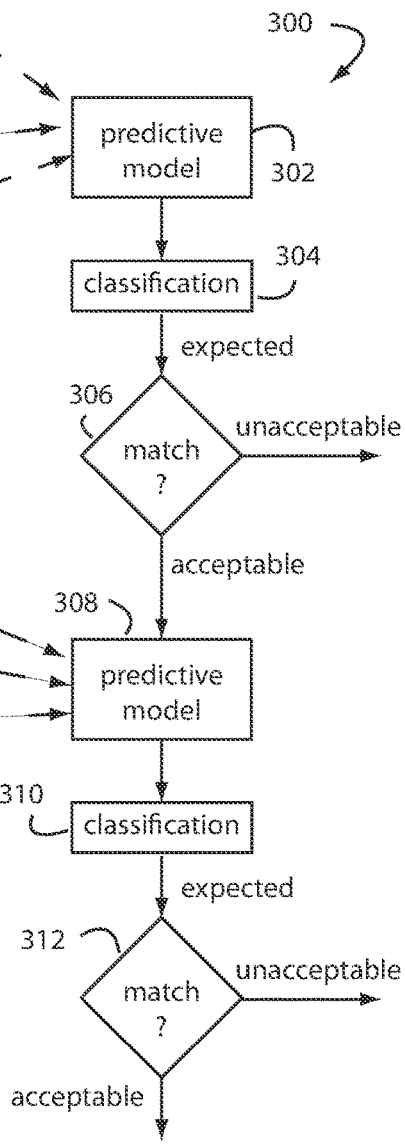
FIG. 3 is a flowchart diagram of a risk and high variance detection method of predicting a DRG from the data available in the method of FIG. 2.

FIG. 3 represents a risk and high variance detection method 300 of predicting a DRG from the data available in method 200 (FIG. 2). Method 300 is a way to contribute to step 108 in method 100. A predictive model 302 is provided the symptoms recorded 202, the diagnostic tests ordered 206, and the diagnostic test results 208 as attributes. From these, the predictive model 302 produces a classification, e.g., a particular DRG class. Such DRG class is the one to be expected given the payment claim attributes and non-claim data that may be available. A test 306 checks if what was claimed as a DRG is what was expected. If not, the payment claim is unacceptable. Otherwise, another predictive model 308 gathers attributes for the diagnostic code 210, any prescriptions 212, and the procedure codes 214. A classification 310 results. A test 312 compares the expected classes to the actual ones claimed. A match indicates an acceptable payment claim.

Figure 4A:
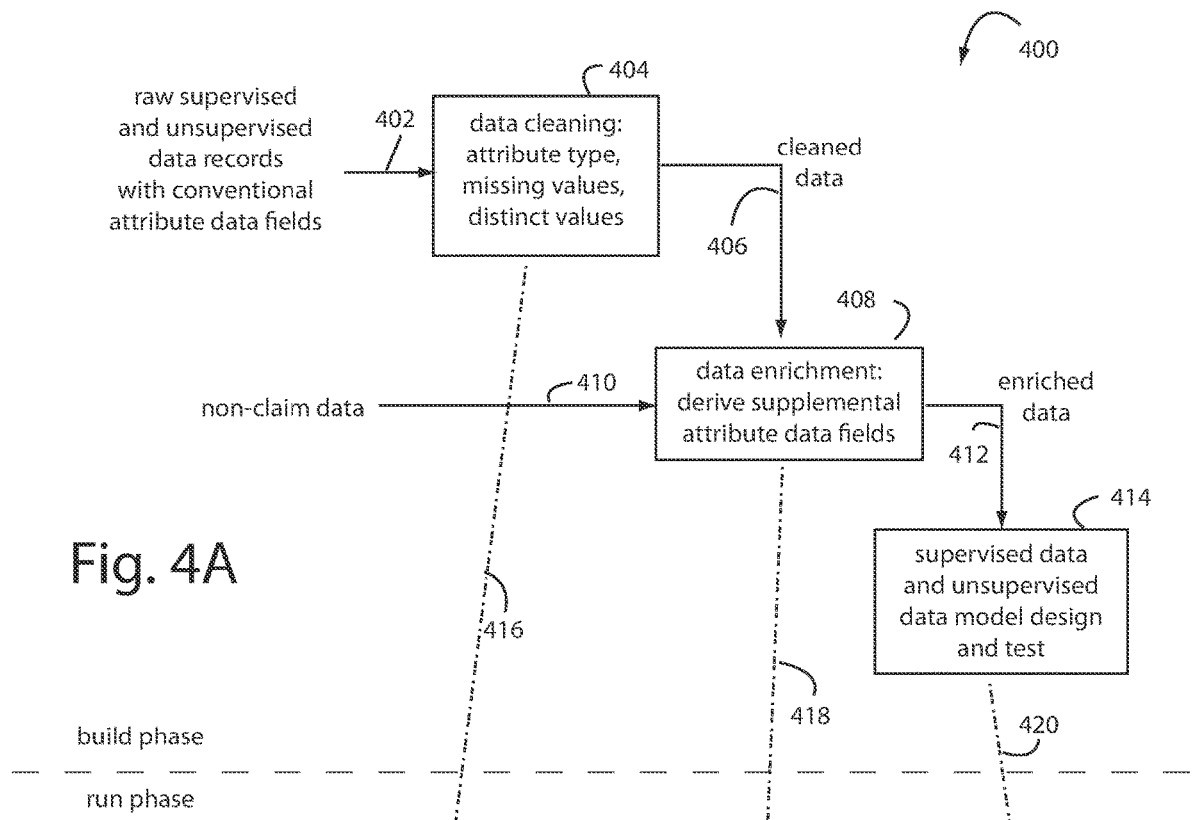
FIG. 4A is flowchart diagram o a method of developing a healthcare predictive model.
Figure 4B:
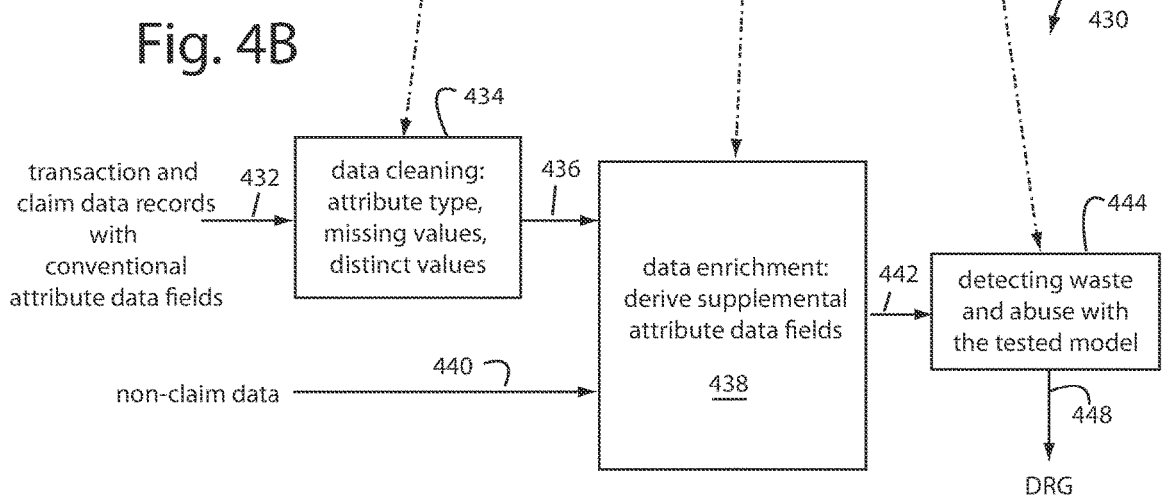
FIG. 4B is flowchart diagram of a method of using the healthcare predictive model of FIG. 4A to detect healthcare payment claim fraud-waste-abuse.

FIGS. 4A and 4B represent both a method 400 of developing a healthcare predictive model, and a method 430 of using such healthcare predictive model to detect healthcare payment claim fraud-waste-abuse. In a build-phase, a database of raw supervised and unsupervised data records 402 with conventional attribute data fields are forwarded to a processor with an algorithm 404 that does data cleaning by inspecting each data field of each data record for attribute type (symbolic or numeric), missing values, and distinct number of values. Such data cleaning is fully described in my recent U.S. patent application, Ser. No. 14/935,742, filed Nov. 9, 2015, and titled, DATA CLEAN-UP METHOD FOR IMPROVING PREDICTIVE MODEL TRAINING. Such Application is incorporated herein, in full, by reference. A cleaned data 406 results that is used by a processor with an algorithm 408 that does data enrichment by deriving supplemental data fields with non-claim data 410.

The data enrichment algorithm 408 is more fully described in my recent U.S. patent application, Ser. No. 14/941,586, filed Nov. 9, 2015, and titled, METHOD OF OPERATING ARTIFICIAL INTELLIGENCE MACHINES TO IMPROVE PREDICTIVE MODEL TRAINING AND PERFORMANCE. Such Application is incorporated herein, in full, by reference. The non-claim data 410 represents facts already known about the healthcare provider submitting the payment claim record and/or details related to other claim attributes.

An enriched data 412 results that is used by a processor with an algorithm 414 that builds decision trees, case-based reasoning logic, smart agent profiles (for every healthcare provider and payment claim attribute), and other predictive models as detailed in the two Patent Applications just mentioned.

Instructions 416, 418, and 420, respectively describe how to structure run-phase data cleaning, data enrichment, and predictive models.

In a run-phase, as represented more fully in FIG. 1, a stream 432 of transaction and claim data records with conventional attribute data fields is stored in a computer memory device and the forwarded to a processor with an algorithm 434 that does the data cleaning outlined in instructions 416. Each cleaned data record 436 is then enhanced by a processor with an algorithm 438 that uses non-claim data to derive new data fields according to instructions 418. Each enhanced data record 442 is then tested by a processor with an algorithm 444 that implements the predictive models outlined in instructions 420. Each enhanced data record 442 produces a DRG 448 that is matched to what the healthcare provider actually coded as their DRG for payment claim.

Step 102 in FIG. 1 collects and organizes data records of incoming streams of healthcare payment claims. Such claims typically have a predefined fixed data field layout, as in the following Table.

Data Layout

| Variable Name | Definition |
| --- | --- |
| IDC | Unique identifier |
| DATE_ADM | Date patient was admitted |
| Date_DISCHARGE | Date patient was discharged |
| SOURCE | Source of the admission |
| TYPE | Describes the admission of the patient to the facility |
| Status_DIS | Patient's destination upon discharge |
| Sex | Patient gender |
| AGE | Patient age in years |
| DOB | Patient date of birth |
| REIMB | The dollar amount paid to the provider for that particular DRG |
| TOTACHRG | Total charge amount—the dollar amount charged by the facility for that particular DRG |
| DRG | Diagnosis Related Group—a code that organizes diagnoses and procedures into clinically cohesive groups that demonstrate similar consumption of hospital resources |
| Diagnosis1 | Primary diagnosis code |
| Diagnosis2 | Secondary diagnosis code |
| Diagnosis3 | Third diagnosis code |
| Diagnosis4 | Fourth diagnosis code |
| Diagnosis5 | Fifth diagnosis code |
| Procedure1 | Primary procedure |
| Procedure2 | Secondary procedure code |
| Procedure3 | Third procedure code |

Each Claim includes data fields for five-digit diagnosis codes and four-digit procedure codes.

Detection of up-coding fraud includes analyzing symptoms and test results. Detecting upcoding fraud is done with a processor and an algorithm that tests each primary diagnosis for cause-and-effect.

Below are some examples of DRGs upcoding:

DRG 475 (respiratory system diagnosis with ventilator support) vs. DRG 127 (heart failure and shock)
Principle diagnosis of respiratory failure (518.81) with a secondary diagnosis of congestive heart failure (428.0) and a procedure code of 96.70, 96.71 or 96.72 (continuous mechanical ventilation).
The hospital bills the respiratory failure as the principal diagnosis but the respiratory failure was due to the patient's congestive heart failure, which by coding guidelines should have been the principal diagnosis
DRG 287 (skin grafts and wound debridement for endocrine, nutritional and metabolic disorders) vs. DRG 294 (diabetes, age greater than 35) or DRG 295 (diabetes, age 0-35)
Principal diagnosis of diabetes mellitus (250.xx) with a principal procedure of excisional debridement of wound, infection or burn (86.22).
The hospital bills for the excisional debridement of a wound (86.22) when, in fact, a non-excisional debridement (86.28) was performed on the patient. This changes the DRG to 294 or 295 (depending on the age of the patient).
DRG 297 (nutritional and miscellaneous metabolic disorders, age greater than 17) and 320 (kidney and urinary tract infections, age greater than 17) vs. DRG 383 (other antepartum diagnoses with medical complications)
  Non-primary diagnosis of pregnancy (V222).
  The hospital bills for dehydration, urinary tract infection or other disorder when, in fact, the primary diagnosis is complications of pregnancy.
DRG 182 (esophagitis, gastroenteritis and miscellaneous digestive disorders, age greater than 17) vs. DRG 383 (other antepartum diagnoses with medical complications)
Non-primary diagnosis of V222 (pregnancy) and a length of stay one day or less.

-continued

Figure 5A:
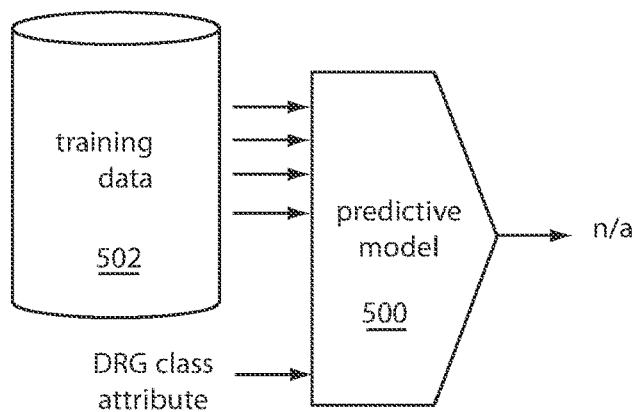
FIGS. 5A, 5B, and 5C are diagrams representing how a predictive model is trained with a learning database and tested with a testing database before being put to use as in FIG. 1.
Figure 5B:
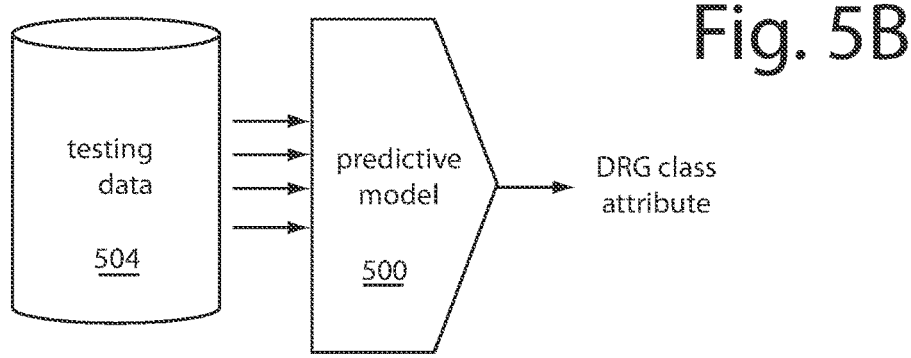
Figure 5C:
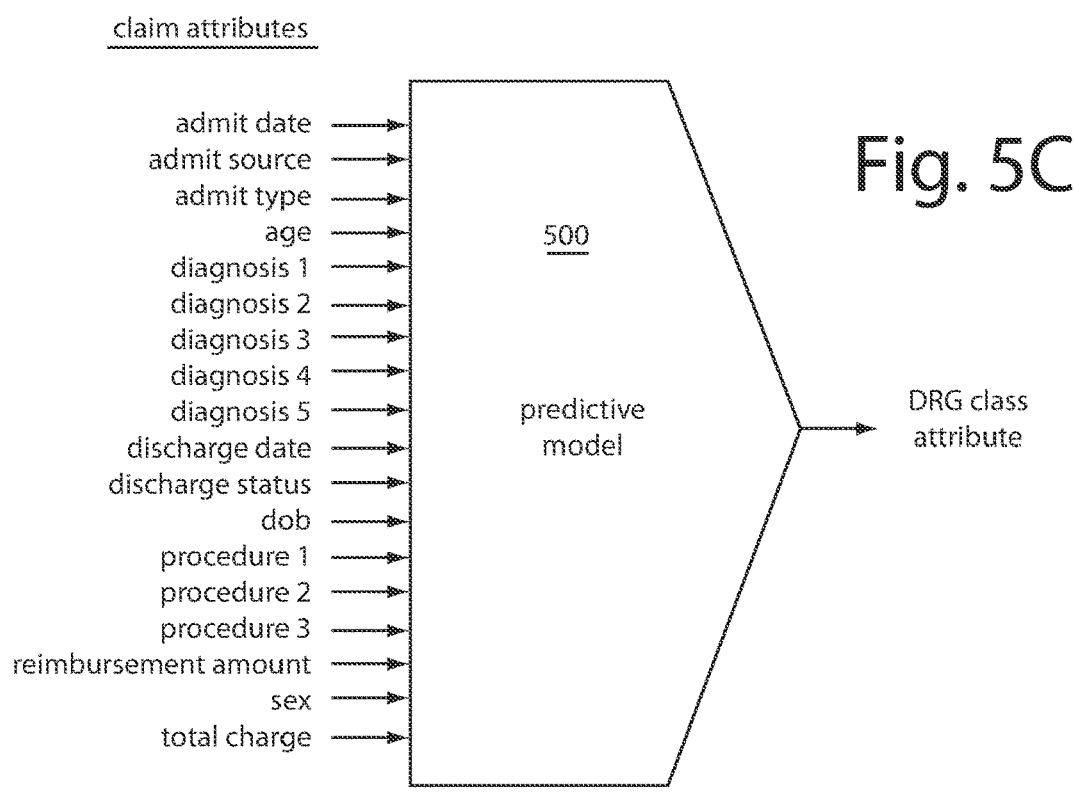

The hospital bills for gastroenteritis or other disorder when, in fact, the primary diagnosis is complications of pregnancy.
DRG 416 (septicemia, age greater than 17) and 417 (septicemia, age 0-17) and if:
The reimbursement amount is between $Amount1 and $Amount2 and is X times the total charge;

FIGS. 5A, 5B, and 5B represent how a predictive model 500 is trained with a learning database 502 and tested with a testing database 504.

For example, a learning database of historical data has 46,933 records and a testing database has 56,976 Records. The first database includes one extra attribute which is used for learning the correct class.

The DRG (Diagnostic Related Group) class attribute is the output that defines what the model will predict. The others attributes are its inputs: they are used to create the model.

Record Example

| | |
|---|---|
| ADMIT DATE | Dec. 3, 2014 |
| ADMIT SOURCE | 5 |
| ADMIT TYPE | 2 |
| AGE | 52 |
| DIAGNOSIS 1 | 51889 |
| DIAGNOSIS 2 | 78632 |
| DIAGNOSIS 3 | 2863 |
| DIAGNOSIS 4 | 5849 |
| DIAGNOSIS 5 | 9976 |
| DISCHARGE DATE | Dec. 23, 2014 |
| DISCHARGE STATUS | 20 |
| DOB | Dec. 26, 1962 |
| PROCEDURE 1 | 9672 |
| PROCEDURE 2 | 3404 |
| PROCEDURE 3 | 3891 |
| REIMBURSEMENT AMOUNT | 2203 |
| SEX | F |
| TOTCHRG | 27200 |

Unsupervised Learning of Normal and Abnormal Behavior

Each field or attribute in a data record is represented by a corresponding smart-agent. Each smart-agent representing a field will build what-is-normal (normality) and what-is-abnormal (abnormality) metrics regarding other smart-agents.

Apparatus for creating smart-agents is supervised or unsupervised. When supervised, an expert provides information about each domain. Each numeric field is characterized by a list of intervals of normal values, and each symbolic field is characterized by a list of normal values. It is possible for a field to have only one interval. If there are no intervals for an attribute, the system apparatus can skip testing the validity of its values, e.g., when an event occurs.

As an example, a doctor (expert) can give the temperature of the human body as within an interval [35° C. 41° C.], and the hair colors can be {black, blond, red}.
1) For each field "a" of a Table:
  i) Retrieve all the distinct values and their cardinalities and create a list "La" of couples (vai, nai);
  ii) Analyze the intermediate list "La" to create the list of intervals of normal values Ia with this method:
    (a) If "a" is a symbolic attribute, copy each member of "La" into Ia when nai is superior to a threshold $\Theta_{min}$;
  (b) If "a" is a numeric attribute:
    1. Order the list "La" starting with the smallest values "va";
    2. While La is not empty;
      i. Remove the first element ea=(val, nal) of "La"
      ii. Create an interval with this element: I'=[val, val]
      iii. While it is possible, enlarge this interval with the first elements of "La" and remove them from "La": l'=[val, vak]. The loop stops before the size of the interval vak-val becomes greater than a threshold $\Theta_{dist}$.
  (c) given: na'=nal+ . . . +nak
  (d) If na' is superior to a threshold $\Theta$min, Ia=I' otherwise, Ia=Ø; iii) If Ia is not empty, save the relation (a, Ia).

An unsupervised learning process uses the following algorithm:

$\Theta_{min}$ represents the minimum number of elements an interval must include. This means that an interval will only be take into account if it encapsulates enough values, so its values will be considered normal because frequent;
the system apparatus defines two parameters that is modified:
the maximum number of intervals for each attribute $n_{max}$;
the minimum frequency of values in each interval $f_{Imin}$;
$\Theta_{min}$ is computed with the following method:
$\Theta_{min} = f_{Imin}$*number of records in the table.
$\Theta_{dist}$ represents the maximum width of an interval. This prevents the system apparatus from regrouping some numeric values that are too disparate. For an attribute a, let's call mina the smallest value of a on the whole table and maxa the biggest one. Then:

$\Theta_{dist} = (maxa - mina)/n_{max}$

For example, consider a numeric attribute of temperature with the following values:

| 75 | 80 | 85 | 72 | 69 | 72 | 83 | 64 | 81 | 71 | 65 | 75 | 68 | 70 |
|---|---|---|---|---|---|---|---|---|---|---|---|---|---|

The first step is to sort and group the values into "La": "La"={(64, 1) (65, 1) (68, 1) (69, 1) (70, 1) (71, 1) (72, 2) (75, 2) (80, 1) (81, 1) (83, 1) (85, 1)}
Then the system apparatus creates the intervals of normal values:
Consider $f_{Imin}$=10% and $n_{max}$=5 then $\Theta_{min}$=1.4 and $\Theta_{dist}$=(85−64)/5=4.2

$Ia = \{[64,68][69,72][75,80,83]\}$

The interval [85, 85] was removed because its cardinality (1) is smaller than $\Theta_{min}$.

When a new event occurs, the values of each field are verified with the intervals of the normal values it created, or that were fixed by an expert. It checks that at least one interval exists. If not, the field is not verified. If true, the value inside is tested against the intervals, otherwise a warning is generated for the field.

During creation, dependencies between two fields are expressed as follows:
When the field 1 is equal to the value v1, then the field 2 takes the value v2 in significant frequency p.
Example: when species is human the body_temperature is 37.2° C. with a 99.5% accuracy.
Given cT is the number of records in the whole database. For each attribute X in the table:

Retrieve the list of distinct values for X with the cardinality of each value:

$$Lx=\{(x1,cx1), \ldots (xi,c_{xi}), \ldots (xn,cxn)\}$$

For each distinct value xi in the list:
Verify if the value is typical enough: $(c_{xi}/cT) > \Theta x$?
If true, for each attribute Y in the table, Y≠X Retrieve the list of distinct values for Y with the cardinality of each value:

$$Ly=\{(y1,cy1), \ldots (yj,c_{yj}), \ldots (yn,cyn)\}$$

For each value yj;
Retrieve the number of records $c_{ij}$ where (X=xi) and (Y=yj). If the relation is significant, save it: if $(c_{ij}/c_{xi}) > \Theta xy$ then save the relation [(X=xi)⇒(Y=yj)] with the cardinalities $c_{xi}$, $c_{yj}$ and $c_{ij}$.
The accuracy of this relation is given by the quotient $(c_{ij}/c_{xi})$
Verify the coherence of all the relations: for each relation [(X=xi)⇒(Y=yj)] (1)
Search if there is a relation [(Y=yj)⇒(X=xk)] (2)
If xi≠xk remove both relations (1) and (2) from the model otherwise it will trigger a warning at each event since (1) and (2) cannot both be true.

To find all the dependencies, the system apparatus analyses a database with the following algorithm:
The default value for Θx is 1%: the system apparatus will only consider the significant value of each attribute.
The default value for Θxy is 85%: the system apparatus will only consider the significant relations found.
A relation is defined by: $(Att_1=v_1) \Rightarrow (Att_2=v_2)$ (eq).
All the relations are stored in a tree made with four levels of hash tables, e.g., to increase the speed of the system apparatus. A first level is a hash of the attribute's name (Att1 in eq); a second level is a hash for each attribute the values that imply some correlations (v1 in eq); a third level is a hash of the names of the attributes with correlations (Att2 in eq) to the first attribute; a fourth and last level has values of the second attribute that are correlated (v2 in eq).
Each leaf represents a relation. At each leaf, the system apparatus stores the cardinalities $c_{xi}$, $c_{yj}$ and $c_{ij}$. This will allow the system apparatus to incrementally update the relations during its lifetime. Also it gives:
the accuracy of a relation: $c_{ij}/c_{xi}$;
the prevalence of a relation: $c_{ij}/cT$;
the expected predictability of a relation: $c_{yj}/cT$.
Consider an example with two attributes, A and B:

| A | B |
|---|---|
| 1 | 4 |
| 1 | 4 |
| 1 | 4 |
| 1 | 3 |
| 2 | 1 |
| 2 | 1 |
| 2 | 2 |
| 3 | 2 |
| 3 | 2 |
| 3 | 2 |

There are ten records: cT=10.
Consider all the possible relations:

| Relation | $C_{xi}$ | $C_{yi}$ | $C_{ij}$ | $(c_{xi}/c_T)$ | Accuracy | |
|---|---|---|---|---|---|---|
| (A = 1) ⇒ (B = 4) | 4 | 3 | 3 | 40% | 75% | (1) |
| (A = 2) ⇒ (B = 1) | 2 | 2 | 2 | 20% | 100% | (2) |
| (A = 3) ⇒ (B = 2) | 3 | 4 | 3 | 30% | 100% | (3) |
| (B = 4) ⇒ (A = 1) | 3 | 4 | 3 | 30% | 100% | (4) |
| (B = 3) ⇒ (A = 1) | 1 | 4 | 1 | 10% | 100% | (5) |
| (B = 1) ⇒ (A = 2) | 2 | 3 | 2 | 20% | 100% | (6) |
| (B = 2) ⇒ (A = 3) | 4 | 3 | 3 | 40% | 75% | (7) |

With the defaults values for Θx and Θxy, for each possible relation, the first test $(c_{xi}/c_T) > \Theta x$ is successful (since Θx=1%) but the relations (1) and (7) would be rejected (since Θxy=85%).
Then the system apparatus verifies the coherence of each remaining relation with an algorithm:
(A=2)⇒(B=1) is coherent with (B=1)⇒(A=2);
(A=3)⇒(B=2) is not coherent since there is no more relation (B=2)⇒ . . . ;
(B=4)⇒(A=1) is not coherent since there is no more relation (A=1)⇒ . . . ;
(B=3)⇒(A=1) is not coherent since there is no more relation (A=1)⇒ . . . ;
(B=1)⇒(A=2) is coherent with (A=2)⇒(B=1).
The system apparatus classifies the normality/abnormality of each new event in real-time during live production and detection.
For each event couple attribute/value (X, xi):
Looking in the model for all the relations starting by [(X=xi)⇒ . . . ]
For all the other couple attribute/value (Y, $y_j$), Y≠X, of the event:
Look in the model for a relation [(X=$x_i$)⇒(Y=v)];
If $y_j$≠v then trigger a warning "[(X=$x_i$)⇒(Y=$y_j$)] not respected".

Incremental Learning

The system apparatus incrementally learns with new events:
Increment cT by the number or records in the new table T.
For each relation [(X=xi)⇒(Y=yj)] previously created:
Retrieve its parameters: $c_{xi}$, $c_{yj}$ and $c_{ij}$
Increment $c_{xi}$ by the number of records in T where X=$x_i$;
Increment $c_{yj}$ by the number of records in T where Y=$y_j$;
Increment $c_{ij}$ by the number of records in T where [(X=$x_i$)⇒(Y=$y_j$)];
Verify if the relation is still significant:
If $(c_{xi}/c_T) < \Theta_x$, remove this relation;
If $(c_{ij}/c_{xi}) < \Theta_{xy}$, remove this relation.

In general, a process for fraud-waste-abuse protection comprises training a variety of real-time, risk-scoring fraud-waste-abuse models with training data selected for each from a common transaction history that then specialize each member in its overview of a selected vertical claim processing financial transactional channel. The variety of real-time, risk-scoring fraud-waste-abuse models is arranged after the training into a parallel arrangement so that all receive a mixed channel flow of real-time claim data or authorization requests. The parallel arrangement of diversity trained real-time, risk-scoring fraud waste-abuse models is hosted on a network server platform for real-time risk scoring of the mixed channel flow of real-time claim data or authorization requests. Risk thresholds are updated without delay for particular healthcare providers, and other healthcare providers in every one of the parallel arrangement of diversity trained real-time, risk-scoring fraud-waste-abuse models when any one of them detects a suspicious or outright fraudulent-wasteful-abusive claim data or authorization request for the healthcare provider.

Such process for fraud-waste-abuse protection can further comprise steps for building a population of real-time and a long-term and a recursive profile for each the healthcare provider in each the real-time, risk scoring fraud-waste-abuse models. Then during real-time use, maintaining and updating the real-time, long-term, and recursive profiles for each healthcare provider in each and all of the real-time, risk-scoring fraud-waste-abuse models with newly arriving data.

Incremental learning technologies are embedded in the machine algorithms and smart-agent technology. These are continually re-trained with at least one processor and an algorithm that machine-learns from any false positives and negatives that occur to avoid repeating classification errors. Any data mining logic incrementally changes its decision trees by creating a new link or updates any existing links and weights, and any neural networks update a weight matrix, and any case-based reasoning logic update a generic case or creates a new one, and any corresponding smart-agents update their profiles by adjusting a normal/abnormal threshold stored in a memory storage device.

Although particular embodiments of the present invention have been described and illustrated, such is not intended to limit the invention. Modifications and changes will no doubt become apparent to those skilled in the art, and it is intended that the invention only be limited by the scope of the appended claims.

I claim:

1. A computer-implemented method for healthcare fraud detection, comprising, via one or more processors:
    receiving a healthcare payment request corresponding to a healthcare provider;
    matching the healthcare payment request to a smart agent having a profile comprising a representation of historical data of the healthcare provider;
    comparing the contents of at least one data field of the healthcare payment request against the profile of the corresponding smart agent and, based at least in part on the comparison, generating a first output indicative of a determination of likely fraud;
    generating a second smart agent having a second profile by unsupervised clustering of a group of healthcare providers based on at least one claim attribute;
    matching the healthcare payment request to the second smart agent having the second profile;
    comparing the contents of at least one data field of the healthcare payment request against the second profile of the corresponding second smart agent and, based at least in part on the comparison, generating a second output indicative of a determination of unlikely fraud;
    analyzing the first output and the second output and generating a decision on the healthcare payment request based at least in part on the analysis, the analysis including determining that the first output meets a first criteria indicating fraud or abuse, determining that the second output meets a second criteria indicating acceptable behavior within the corresponding group, and determining that the second output overrides the first output,
        wherein the decision comprises an approval decision for the healthcare payment request.

2. The computer-implemented method of claim 1, further comprising updating, via the one or more processors, the second profile to reflect the second output.

3. The computer-implemented method of claim 1, further comprising—
    inputting the contents of at least one data field of the healthcare payment request to a treatment model to produce a predicted diagnostic code,
    comparing the predicted diagnostic code to the healthcare payment request to produce a third output, the decision being based at least in part on the third output.

4. The computer-implemented method of claim 3, wherein—
    comparing the predicted diagnostic code to the healthcare payment request includes determining whether the predicted diagnostic code matches one or both of a prescription and procedure code corresponding to the healthcare payment request,
    the third output is indicative of a determination that the predicted diagnostic code does not match one or both of the corresponding prescription and procedure codes.

5. The computer-implemented method of claim 3, wherein—
    comparing the predicted diagnostic code to the healthcare payment request includes determining whether the predicted diagnostic code matches one or both of an expected diagnostic test and diagnostic test results corresponding to the healthcare payment request,
    the third output is indicative of a determination that the predicted diagnostic code matches one or both of the corresponding expected diagnostic test and diagnostic test results.

6. The computer-implemented method of claim 5, wherein the third output contributes to the override of the first output.

7. At least one network server for healthcare fraud detection, the at least one network server comprising:
    one or more processors;
    non-transitory computer-readable storage media having computer-executable instructions stored thereon, wherein when executed by the one or more processors the computer-readable instructions cause the one or more processors to—
        receive a healthcare payment request corresponding to a healthcare provider;
        match the healthcare payment request to a smart agent having a profile comprising a representation of historical data of the healthcare provider;
        compare the contents of at least one data field of the healthcare payment request against the profile of the corresponding smart agent and, based at least in part on the comparison, generate a first output indicative of a determination of likely fraud;
        generate a second smart agent having a second profile by unsupervised clustering of a group of healthcare providers based on at least one claim attribute;
        match the healthcare payment request to the second smart agent having the second profile;
        compare the contents of at least one data field of the healthcare payment request against the second profile of the corresponding second smart agent and, based at least in part on the comparison, generate a second output indicative of a determination of unlikely fraud;
    analyze the first output and the second output and generate a decision on the healthcare payment request based at least in part on the analysis, the analysis including determining that the first output meets a first criteria indicating fraud or abuse, determining that the second output meets a second criteria indicating acceptable behavior within the corresponding group, and determining that the second output overrides the first output, wherein the decision comprises an approval decision for the healthcare payment request.

8. The at least one network server of claim 7, wherein, when executed by the one or more processors, the computer-readable instructions further cause the one or more processors to update the second profile to reflect the second output.

9. The at least one network server of claim 7, wherein, when executed by the one or more processors, the computer-readable instructions further cause the one or more processors to—
input the contents of at least one data field of the healthcare payment request to a treatment model to produce a predicted diagnostic code,
compare the predicted diagnostic code to the healthcare payment request to produce a third output, the decision being based at least in part on the third output.

10. The at least one network server of claim 9, wherein—
comparing the predicted diagnostic code to the healthcare payment request includes determining whether the predicted diagnostic code matches one or both of a prescription and procedure code corresponding to the healthcare payment request,
the third output is indicative of a determination that the predicted diagnostic code does not match one or both of the corresponding prescription and procedure codes.

11. The at least one network server of claim 9, wherein—
comparing the predicted diagnostic code to the healthcare payment request includes determining whether the predicted diagnostic code matches one or both of an expected diagnostic test and diagnostic test results corresponding to the healthcare payment request,
the third output is indicative of a determination that the predicted diagnostic code matches one or both of the corresponding expected diagnostic test and diagnostic test results.

12. The at least one network server of claim 11, wherein the third output contributes to the override of the first output.

13. Non-transitory computer-readable storage media having computer-executable instructions for healthcare fraud detection, wherein when executed by at least one processor the computer-readable instructions cause the at least one processor to:
receive a healthcare payment request corresponding to a healthcare provider;
match the healthcare payment request to a smart agent having a profile comprising a representation of historical data of the healthcare provider;
compare the contents of at least one data field of the healthcare payment request against the profile of the corresponding smart agent and, based at least in part on the comparison, generate a first output indicative of a determination of likely fraud;
generate a second smart agent having a second profile by unsupervised clustering of a group of healthcare providers based on at least one claim attribute;
match the healthcare payment request to the second smart agent having the second profile;
compare the contents of at least one data field of the healthcare payment request against the second profile of the corresponding second smart agent and, based at least in part on the comparison, generate a second output indicative of a determination of unlikely fraud;
analyze the first output and the second output and generate a decision on the healthcare payment request based at least in part on the analysis, the analysis including determining that the first output meets a first criteria indicating fraud or abuse, determining that the second output meets a second criteria indicating acceptable behavior within the corresponding group, and determining that the second output overrides the first output, wherein the decision comprises an approval decision for the healthcare payment request.

14. The computer-readable storage media of claim 13, wherein, when executed by the at least one processor, the computer-readable instructions further cause the at least one processor to update the second profile to reflect the second output.

15. The computer-readable storage media of claim 13, wherein, when executed by the at least one processor, the computer-readable instructions further cause the at least one processor to—
input the contents of at least one data field of the healthcare payment request to a treatment model to produce a predicted diagnostic code,
compare the predicted diagnostic code to the healthcare payment request to produce a third output, the decision being based at least in part on the third output.

16. The computer-readable storage media of claim 15, wherein—
comparing the predicted diagnostic code to the healthcare payment request includes determining whether the predicted diagnostic code matches one or both of a prescription and procedure code corresponding to the healthcare payment request,
the third output is indicative of a determination that the predicted diagnostic code does not match one or both of the corresponding prescription and procedure codes.

17. The computer-readable storage media of claim 15, wherein—
comparing the predicted diagnostic code to the healthcare payment request includes determining whether the predicted diagnostic code matches one or both of an expected diagnostic test and diagnostic test results corresponding to the healthcare payment request,
the third output is indicative of a determination that the predicted diagnostic code matches one or both of the corresponding expected diagnostic test and diagnostic test results.

* * * * *